(12) United States Patent
Erneux et al.

(10) Patent No.: US 6,703,215 B2
(45) Date of Patent: Mar. 9, 2004

(54) INHIBITORS OF THE INOSITOL POLYPHOSPHATE 5-PHOSPHATASE SHIP2 MOLECULE

(75) Inventors: Christopher Erneux, Rhode-Saint Geneso (BE); Stephane Schurmans, Wezembeek-Oppem (BE)

(73) Assignee: Euroscreen, s.a., Gosselies (BE)

( * ) Notice: Subject to any disclaimer, the term of this patent is extended or adjusted under 35 U.S.C. 154(b) by 0 days.

(21) Appl. No.: 09/922,543

(22) Filed: Aug. 3, 2001

(65) Prior Publication Data

US 2002/0106713 A1 Aug. 8, 2002

Related U.S. Application Data

(63) Continuation-in-part of application No. PCT/BE00/00132, filed on Oct. 31, 2000.

(51) Int. Cl.[7] .......................... C12Q 1/42; C12N 15/09; C12N 9/12; C07H 21/04
(52) U.S. Cl. ...................... 435/21; 435/69.2; 435/194; 536/23.2
(58) Field of Search .................... 435/21, 69.2, 194; 536/23.2

(56) References Cited

U.S. PATENT DOCUMENTS

| 5,023,248 A | 6/1991 | Siren ........................ 514/103 |
| 5,885,980 A | 3/1999 | Gutierrez et al. ........... 514/186 |

FOREIGN PATENT DOCUMENTS

| JP | 05 194580 | 8/1993 |
| WO | WO 97/12039 | 4/1997 |
| WO | WO 97/22716 | 6/1997 |
| WO | WO 98/11901 | 3/1998 |

OTHER PUBLICATIONS

Sequence Alignment between—Accession No. EMBL Y14385 in Pesesse et al. Biochem. Biophys. Res. Com. 239, 697–700 (1997) and Applicants' SEQ ID NO : 1.*

Pesesse, et al. (1997). "Identification of a Second SH2–Domain–Containing Protein Closely Related to the Phosphatidylinositol Polyphosphate 5–Phosphatase SHIP," *Biochemical and BioPhysical Research Communications* 239:697–700.

Presesse, et al. (1998). "The SH2 domain containing inositol 5–phosphatase SHIP2 displays phosphatidylinositol 3,4,5–trisphosphate and inositol 1,3,4,5–tetrakisphosphate 5–phosphatase activity," *FEBS Letters* 437:301–303.

Schurmans, et al. (1999). "The Mouse SHIP2 (Inppl1) Gene: Complementary DNA, Genomic Structure, Promoter Analysis, and Gene Expression in the Embryo and Adult Mouse," *Genomics* 62:260–271.

Sasaoka, et al. (1999). "Molecular Cloning and Characterization of Rat SHIP2 in the Regulation of Insulin Action," *Diabetes* 48(Supp. 1):A60.

* cited by examiner

*Primary Examiner*—Tekchand Saidha
(74) *Attorney, Agent, or Firm*—Kathleen M. Williams; Palmer & Dodge LLP

(57) ABSTRACT

The present invention is related to an inhibitor of the inositol polyphosphate 5-phosphatase SHIP2 protein or its encoding nucleotide sequence identified by SEQ ID NO. 1 or of SHIP2 mRNA expression. The present invention is also related to a pharmaceutical composition comprising the inhibitor and an adequate pharmaceutically acceptable carrier or diluent and to a non-human knock-out mammal comprising homozygously or heterozygously a partial or total deletion in its genome of the inositol polyphoshate 5-phosphatase SHIP2 nucleotide sequence.

4 Claims, 7 Drawing Sheets

INHIBITORS OF THE INOSITOL POLYPHOSPHATE 5-PHOSPHATASE SHIP2 MOLECULE

This is a continuation-in-part of PCT/BE00/00132, filed Oct. 31, 2000.

FIELD OF THE INVENTION

The present invention relates generally to the fields of diabetes. More particularly, it concerns the identification of genes and proteins responsible for diabetes and to their inhibitors for use in therapeutics.

BACKGROUND OF THE INVENTION AND STATE OF THE ART

Insulin is the primary hormone involved in glucose homeostasis. Partial or total deficiency in insulin secretion or action leads to impaired glucose metabolism and diabetes.

Diabetes is a major cause of health difficulties in the world. Non-insulin dependent diabetes mellitus (NIDDM also referred to as Type 2 diabetes) is a major public health disorder of glucose homeostasis affecting about 5% of the general population in the United States. The causes of the fasting hyperglycemia and/or glucose intolerance associated with this form of diabetes are not well understood.

Clinically, NIDDM is a heterogeneous disorder characterised by chronic hyperglycemia leading to progressive micro- and macro-vascular lesions in the cardiovascular, renal and visual systems as well as diabetic neuropathy. For these reasons, the disease may be associated with early morbidity and mortality.

In the field of genomics, various mutations in the diabetes susceptibility genes were identified, for instance in the hepatocyte nucleotide factor genes family (HNF-1, HNF-4 and HNF-6) as described in documents WO98/11254 and WO98/23780.

The role of said genes in biochemical pathways affecting synthesis or secretion of insulin by the beta cells of Langerhans islets has been identified by the phenotype analysis of knock-out mice wherein said genes or portions thereof have been deleted from their genome.

Said knock-out mammal are thereafter used as models for the identification of new compounds or new methods of treatment which could be used for decreasing the symptoms resulting from diabetes.

It is also possible to use the corresponding identified genes which will be present in a sufficient amount in a pharmaceutical composition for the treatment and/or the prevention of said disease.

However, in this field, it exists a need for the identification of new target and biological pathways which could be used for improving the treatment and/or the prevention of diabetes.

Type 2 SH2-domain-containing inositol polyphosphate 5-phosphatase or SHIP2 is closely linked to phosphatidylinositol 3'-kinase and Shc/ras/MAP kinase-mediated signaling events in response to stimulation by specific growth factors.

The structure of SH2-domain containing enzymes and presenting a phosphatase catalytic activity has been already described by Pesesse et al. (1997 and 1998) and Erneux et al. (1998).

It is known that said SH2-domain containing proteins shows similarity with another known inositol polyphosphate 5-phosphatase identified as molecule SHIP1 and shows also 99% identity to a previously reported sequence (INPPL-1). INPPL-1 however, did not contain an SH2 domain.

Said new sequence will be identified hereafter as the molecule SHIP2. The other known inositol 5-phosphatase SHIP1 has been the subject of an intensive research because it may be possibly involved in negative Signalling of B immune cells and could be therefore used as target for the screening of new molecules having possibly therapeutical and/or prophylactic properties in the treatment of various immune inflammatory or allergic symptoms and diseases.

Toshiyasusasaoka et al. (Diabetes Vol. 84, No. PPA 60 (1999)(XP 000905226)) describe the cloning characterisation of a rat SHIP2 molecule that does not have the SAM domain present in human SHIP2. They show that overexpression of the SHIP2 molecule inhibits insulin-induced PKB activation by the 5-inositol phosphatase activity of SHIP2. The authors suggest that SHIP2 plays a negative regulatory role in diverse biological action of insulin and that the dual regulation of the SHC-Grb2 complex and downstream molecule of PI3-kinase provides possible mechanisms of SHIP2 molecule to participate in insulin signalling.

The international patent application WO 97/12039 describes the purification and the isolation of the nucleic acid molecules comprising a sequence encoding the SH2-containing inositol-phosphatase, a vector comprising said sequence, a cell transformed by said vector and a purified and isolated SH2-containing inositol-phosphatase molecule expressed by said cell. This document describes also antibodies directed against said protein and a method for identifying a substance capable of binding to said protein.

However, the precise functions of said SH2-domain containing inositol polyphosphate 5-phosphatase SHIP2 has not yet been identified.

SUMMARY OF THE INVENTION

The inventors have discovered unexpectedly that a knock-out mammal, preferably a knock-out mouse, comprising the partial or total deletion (heterozygously or homozygously) of said SH2-domain-containing polyphosphate inositol 5-phosphatase SHIP2 sequence is hypersensitive to insulin (severe postnatal hypoglycaemia and deregulated expression of genes involved in gluconeogenesis).

This increased sensitivity is so important that after two or three days following the birth, the homozygote (SHIP2-/-) mice die from severe hypoglycemia, and that an unpaired glucose tolerance is observed in heterozygote (SHIP2+/-) mice.

In vitro, the absence of one or both normal alleles of the SHIP2 gene is associated with an increased activation of PKB, an effector of PdtIns 3-kinase cascade, and of MAP kinase in response to insulin. These results provide the first direct evidence that SHIP2 is a potent negative regulator of insulin signalling in vivo, and a potential therapeutic target for the treatment of type II diabetes.

A first aspect of the present invention is related to an inhibitor of said inositol polyphosphate 5-phosphatase SHIP2 molecule, preferably a human molecule, said inhibitor being directed against said molecule and being able to reduce or block its activity or expression.

A first preferred example of said inhibitor is an anti-sense RNA (of 8 to 50 bases, preferably from 10 to 30 bases in length) constructed from the complementary sequence of the messenger RNA that can be deduced from the sequence of SHIP2 molecule complementary DNA encoding the sequence (identified hereafter as SEQ ID NO. 1 and by Erneux et al. (1998)) or its complementary strand and which specifically hybridises and inhibits its expression. Said inhibitors can also be a molecule that directly or indirectly decreases SHIP2 mRNA expression (transcription factors) or stability.

A second example of said inhibitor is a mutated SHIP2 molecule or a portion thereof of more than about 30, about 50, about 100 or about 150 amino-acids (negative dominant) that would prevent the natural activity of SHIP2 by competition of the mutated molecule to interacting proteins or receptors involved in insulin production cascade. Preferably, said mutated SHIP2 molecule or portion comprises a mutation in the following amino acid sequence: RTNVPSWCDR (SEQ ID NO: 4), especially one or more mutations, preferably of the following amino acids: S, C, N, D or R of said specific SHIP2 portion sequence. Said mutation(s) affect(s) the catalytic site of the SHIP2 molecule (phosphatase activity), as described in Erneux et al. (1998). Those mutations typically would create dominant negative effects.

Other examples of said inhibitors are substrates of said SHIP2 molecule (being an enzyme) and analogues of its substrates such as the phosphatidylinositol 3,4,5-triphosphate, the inositol 1,3,4,5-tetrakisphosphate, the inositol 1,4,5 triphosphate adenophostin or any available analogue of the inositol phosphate structure including the membrane-permeant esters or phosphatidylinositol 3,4,5-triphosphate that have been used to deliver the phosphatidylinositol 3,4,5-triphosphate across cell membranes.

Said inhibitor can be also a competitive inhibitor, such as the 2,3-biphosphoglycerate, thiol blocking agents or any protein phosphatase inhibitor such as the okadaic acid or the orthovanadate. The inhibitor can be also a specific portion of more than about 30, about 50, about 100 or about 150 amino-acids of the protein structure of said enzyme, preferably a portion comprising the SH2-domain (the first 110 amino acids of the sequence SEQ ID NO. 1, the proline-rich domain (the last 351 amino acids of the sequence SEQ ID NO. 1) or more preferred portions of said sequence which are able to compete with the molecule SHIP2 recruitment to plasma membranes, thereby inhibiting its activity. The term "competitive inhibitor" is well accepted in the art.

The inhibitor could also reduce or block the activity of the SHIP2 molecule, or reduces the expression of the SHIP2 mRNA.

The inhibitor or a pharmaceutical composition comprising an acceptable carrier or diluent or the inhibitor according to the invention, being able to reduce or block the activity of the SHIP2 molecule, increases the sensibility of a patient (including a human) to insulin and could be advantageously used in the treatment or the prevention of type II diabetes and associated diseases.

Another aspect of the present invention is related to a method, kit or apparatus for the detection of known or unknown compounds which could be used as inhibitors of said inositol polyphosphate 5-phosphatase SHIP2 molecule. Said method comprises the steps of submitting said unknown compounds to an assay based upon the analysis of SHIP2 molecule activity. Said assay, is advantageously performed on a molecular construct containing the catalytic domain of the SHIP2 enzyme (for the corresponding human SHIP2 molecule identified in the enclosed sequence SEQ ID NO. 1, this ranges from the amino acid 427 to the amino acid 729 or one or more specific portions of said catalytic domain), said construct being expressed in a micro-organism, preferably in E. coli, or in a cell line and the assay comprising the means for quantifying the hydrolysis of inositol 1,3,4,5-tetrakisphosphate and the production of inositol 1,3,4-triphosphate. The expression of SHIP2 in bacteria E. coli has been described in Pesesse et al., 1998.

The kit, apparatus and method according to the invention comprise substrates commercially available. The assay according to the invention could also be based upon a quantification of the hydrolysis of phosphatidylinositol 3,4,5-triphosphate followed by thin layer chromatography analysis. A decrease in the amount of a hydrolysis product of 5-phosphatase activity refers to 10% or greater decrease in a signal analysed by the thin layer chromatography in the presence of an inhibitor relative to its absence.

Another analysis of possible inhibitors of the SHIP2 molecule activity is based upon the inhibition of SHIP2 phosphorylation on tyrosine, because this index of activation has been shown to be crucial in the activation process and the insulin sensitive pathways. The SHIP2 molecule is purified and tested for its phosphorylation by Western blot analysis with anti-phosphotyrosine antibody which could be used also as an inhibitor according to the invention.

Another analysis of possible inhibitors of SHIP2 molecules is based upon the reduction or inhibition of SHIP2 mRNA expression, because reduced expression of SHIP2 mRNA in viva is associated with increased isulin sensitivity. SHIP2 promoter region or untranslated regions (5' or 3') of SHIP2 cDNA are linked with a reporter gene (luciferase, CAT, . . . ) in a plasmid vector and transfected into cells in culture. Compounds to be tested are added or not to the cells, and reporter gene activity is recorded to fond out compounds that reduce reporter gene activity, i.e. compounds that act throught the promoter, 5' or 3' untranslated regions of SHIP2 sequences to reduce the production of the protein. A reduction of expression refers to a 10% or greater decrease in SHIP2 mRNA level in the presence of an inhibitor relative to its absence.

A last aspect of the present invention is related to a non-human knock-out mammal comprising (homozygously or heterozygously) a partial or total deletion (in its genome) of the genetic sequence encoding the inositol polyphosphate 5-phosphatase SHIP2 enzyme, said knock-out mammal being hypersensitive to insulin and which could be used as a model for the study of diseases like severe hypoglycaemia in human newborn, or unpaired glucose tolerance in adult humans as well as the study of their treatment. Said genetic sequence encodes the inositol polyphosphate 5-phosphatase SHIP2 molecule (enzyme) identified hereafter as SEQ ID NO. 1 and described by Pesesse et al. (1997).

Said non-human knock-out mammal is preferably a knock-out mouse, obtained by techniques well-known by a person skilled in the art. Said mammal is preferably obtained by a genetic modification, a partial or total deletion in the wild type sequence through the integration of a foreigner nucleic acid sequence. Said genetically modified sequence is incorporated in a vector or electroporated and reintroduced in an embryonic stem cell (ES) for which cellular clones are selected before the integration preferably in a Swiss pseudo-gravide morula-embryo according to the technique described by Carmeliet et al. (1996), allowing thereafter the selection of mice comprising the heterozygous modification of said wild-type sequence and after crossing homozygously genetically modified mice.

DETAILED DESCRIPTION OF THE INVENTION

Figure 1A:
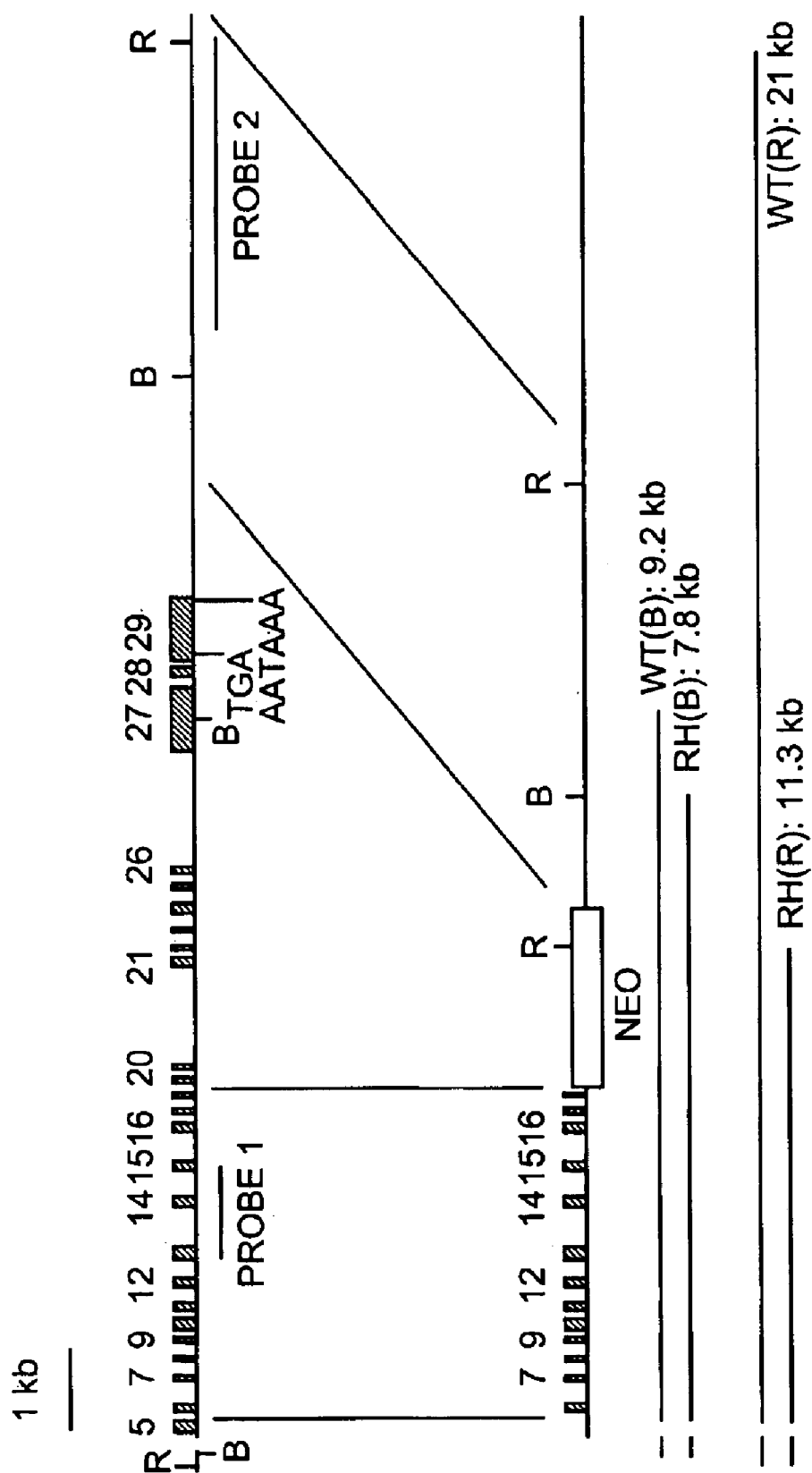
FIG. 1 represents the targeted disruption of SHIP2 gene. (a, The wild type allele (top) and the targeting vector (bottom) are represented (exons, closed boxes), as well as the 2 probes used in Southern analysis and the DNA fragments generated after digestion with EcoRI and BamHI. R: EcoRI; B: BamHI. b, Southern blot analysis of wild type (+/+) and recombinant (+/−) ES cells, as well as of progeny of a heterozygote cross. Genomic DNA was digested with either EcoRI or BamHI and hybridized with probe 1. c, Northern blot analysis of mRNA (2 µg/lane) isolated from SHIP2$^{+/+}$, SHIP2$^{+/-}$ and SHIP2$^{-/-}$ MEFs hybridized with a mouse SHIP2 or actin cDNA fragment as probes. d, Western blot analysis of proteins (100 µg/lane) isolated from SHIP2$^{+/+}$, SHIP2$^{+/-}$ and SHIP2$^{-/-}$ MEFs probed with a rabbit anti-SHIP2 antibody. A single signal at 160 KDa is observed.)
Figure 1B:
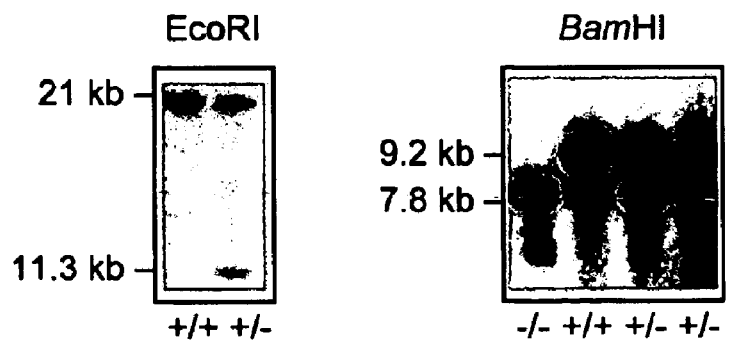

In order to characterize SHIP2 molecule functions in vivo, the inventors have generated and analysed a mouse strain deficient from the SH122 gene according to the following preferred method.

Production of SHIP2 Deficient Mice and Genotyping

The targeting vector was constructed by replacing a 7.3 kb genomic fragment containing exons 19–29 and the polyadenylaticn signal of the mouse SHIP2 gene by a neomycin resistance cassette (Schurmans et al. (1999)). The cassette was flanked by a 4.0 kb and a 5.5 kb mouse genomic DNA fragments at the 5' and 3' regions, respectively. R1 ES cells were electroporated with the targeting plasmid linearized by SalI. Homologous recombination at the SHIP2 locus was confirmed by Southern blotting, and SHIP2$^{+/-}$ ES cells were aggregated with morulae derived from CD1 mice. The resulting chimaeric mice transmitted the mutant allele to the progeny. For genotyping, Southern analysis was performed with specific probes (described in FIG. 1a) or by polymerase chain reaction using specific primers to amplify the neo gene and a specific exon deleted in the mutant allele.

Northern and Western Analysis

Messenger RNA was extracted from mouse embryonic fibroblasts (MEF) using a FastTrack kit (Invitrogen), and total RNA was purified from newborn liver and from adult skeletal and cardiac muscles using the RNeasy Mini Kit (Qiagen). 2 µg/lane of mRNA or 20 µg/lane of total RNA were loaded on a 1% agarose gel and transferred to a nylon membrane. The membranes were hybridized with mouse cDNA fragments coding for SHIP2, TAT-5', C/EBPα, C/EBPβ, aldolase B, actin or G-6-Pase as probes. Antisense oligonucleotide probes were used for PEPCK mRNA (5'-CAGACCATTATGCAGCTGAGGAGGCATT-3' (SEQ ID NO: 2)) and 18S RNA (5'-GTGCGTACTTAGACATGCATG-3' (SEQ ID NO: 3)) detection (Lee et al. (1997)). Supernatants of MEF homogenates isolated from SHIP2+/++, SHIP2+/− and SHIP2−/− day 13.5 embryos were analyzed by Western blot. Proteins (100 µg/lane) were separated by SDS-PAGE and transferred to nitrocellulose sheets. Saturation, incubation with rabbit anti-SHIP2 antiserum and ECL detection were performed as described (Bruyns et al. (1999)). For in vivo GLUT4 expression, SHIP2+/+ and SHIP2+/− mice (6–10 week-old) were overnight fasted, anaesthetized and intravenously injected or not with 1 mU/g (body weight) insulin. After 5 min, the skeletal muscles from the hind limbs were removed. A plasma membrane-rich fraction and a total lysate were prepared from myocytes as described (Simpson et al. (1983), Higaki et al. (1999)). Aliquots of proteins (100 µg) were separated by SDS-PAGE and blotted with anti-GLUT4 antibody. Immune complexes were detected by using 1251 protein-A.

Glucose and Insulin Tolerance Tests SHIP2$^{+/+}$ and SHIP2$^{+/-}$ mice (6–10 week-old) were fasted for more than 12 h and intraperitoneally injected with either 1.5 mg/g (body weight) D-glucose or 1 mU/g (body weight) insulin (Actrapid™, Novo Nordisc, Denmark). Blood samples were drawn from the retro-orbital sinus at different time points. Blood glucose concentration was determined enzymatically. Plasma insulin levels were determined using a rat insulin ELISA kit™ (Mercodia AB, Uppsala, Sweden).

In Vivo Treatments with Glucose or Anti-Insulin Antibodies

Newborns received either repeated intraperitoneal injections of D-glucose (7%, 100 µl per injection) during the first 24 hours after birth, or a single intraperitoneal injection of a guinea pig anti-porcine insulin polyclonal Ab (1/800 in 0.9% NaCl, 100 µ; ref AB1295™, Chemicon Int Inc, Temecula, Calif.) within the first postnatal hour. The neutralizing effect of this anti-insulin antibody was demonstrated after injection in adult mice loaded with glucose: significantly increased blood glucose levels were observed after 30 and 60 min, as compared to non-treated or normal guinea pig serum-treated mice.

Output of Insulin From Pancreatic Islet Cells

Pancreatic islets (Malaisse et al. (1984)), prepared by the collagenase procedure from the pancreas of 3–4 mice, were incubated in groups of 8 islets each for 90 min at 37° C. in 1.0 ml of a Hepes- and bicarbonate-buffered medium containing 5 mg/ml bovine serum albumin and, as required, 11.1 mM D-glucose. The insulin released in the medium was measured by radioimmunoassay.

Analysis of Glycogen Synthesis in Isolated Soleus Muscles

The 2 soleus muscles were rapidly isolated from overnight fasted SHIP2$^{+/+}$ or SHIP2$^{+/-}$ mice, and tied to stainless steel clips by the tendons (Stenbit et al. (1996)). All incubations were carried out at 37° C. under an atmosphere of 95% $O_2$:5% $CO_2$ in 1 ml of Krebs-Ringer bicarbonate buffer (pH 7.35) supplemented with 1% bovine serum albumin (Fraction V, pH 7, Intergen) and 2 mM pyruvate. Following a 15 min preincubation without insulin, muscles were incubated for 60 min without or with the indicated concentrations of insulin in the same medium without pyruvate but with 3-[$^3$H]-glucose (5 mM, 1 µCi/ml). Upon completion, muscles were dissolved in 1 N NaOH, and aliquots of the alkaline solution were spotted onto Whatmann papers. Papers were dropped into ice-cold 60% ethanol, and washed extensively (three washes of 20 min each) in 60% ethanol before counting. All results were expressed per mg muscle protein (determined by the well-known Pierce assay).

Results

Figure 1C:
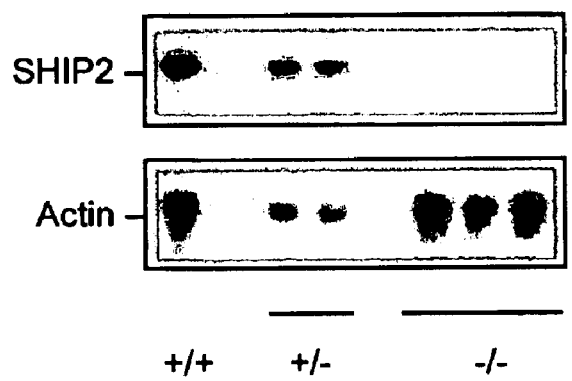
Figure 1D:
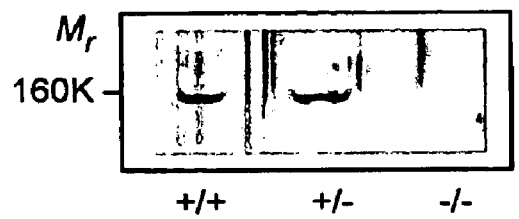

After electroporation of embryonic stem (ES) cells with the targeting vector, the inventors have used Southern blotting and two different probes and restriction enzymes in order to identify recombinant clones with a 7.3 kb genomic DNA deletion on one allele of the SHIP2 gene (FIG. 1a, b). Crossing of chimeric males with C57BL/6 females resulted in F1 heterozygous (SHIP2$^{+/-}$) mice that have no obvious abnormalities. The body weight at 8 weeks, life expectancy and spontaneous tumor incidence were not significantly different from wild-type SHIP2$^{+/+}$ mice. F1 SHIP2$^{+/-}$ mice were then intercrossed and 182 viable offspring were genotyped at birth; of these, 47 (26%) were SHIP2$^{+/+}$, 94 (51%) SHIP2$^{+/-}$ and 41 (22%) SHIP2$^{-/-}$. These frequencies were within Mendelian expectations for transmission of an autosomal gene, and suggest that disruption of both SHIP2 alleles does not cause embryonic lethality. Day 13.5 embryo-derived mouse embryonic fibroblasts (MEF) were analyzed to confirm the reduced levels and the complete absence of SHIP2 mRNA (FIG. 1c) or protein (FIG. 1d) in SHIP2$^{+/-}$ and SHIP2$^{-/-}$ mice, respectively.

At birth, SHIP2$^{-/-}$ mice were phenotypically indistinguishable from their littermates; most of them were able to feed, although progressively less efficiently than SHIP2$^{+/+}$ or SHIP2$^{+/-}$ mice. Close monitoring revealed that SHIP2$^{-/-}$ mice became progressively cyanotic or pale and lethargic within the first 24 hours of life. Some newborn SHIP2$^{-/-}$ pups presented signs of respiratory distress and all failed to gain weight (SHIP2$^{+/+}$: 1.60±0.02 g, SHIP2$^{+/-}$: 1.63±0.04 g and SHIP2$^{-/-}$: 1.20±0.01 g for a typical litter of 10 newborns, 18 hours after birth; Student t test, P<0.005), and died within 3 days after birth. The cause of the respiratory distress observed in some of the SHIP2$^{-/-}$ mice was not a lack of surfactant or an abnormal differentiation of surfactant-producing cells, since the expression of surfactant-associated proteins (SP-A, SP-B and SP-C) and of TTF-1 or C/EBP transcription factors was normal in the lungs of SHIP2$^{-/-}$ mice. Moreover, hematoxylin and eosin staining of SHIP2$^{-/-}$ lung, as well as of brain, heart, thymus, liver, stomach, pancreas, kidney, skin, muscle, spleen, bladder, and small and large intestines sections revealed no particular abnormalities.

Figure 2A:
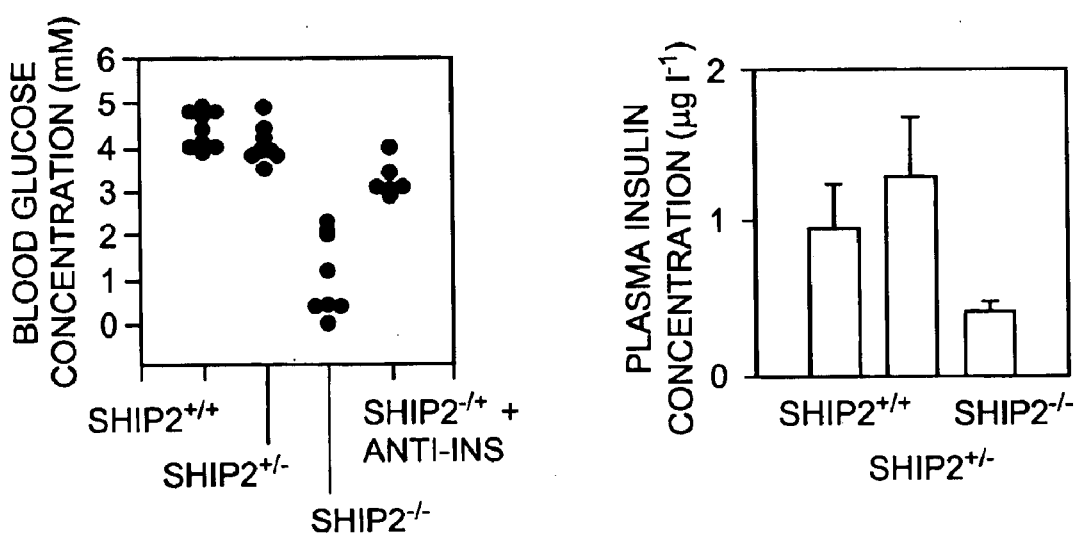
FIG. 2 represents the impaired glucose homeostasis in SHIP2$^{-/-}$ newborns. (a, Blood glucose (top) and plasma insulin (bottom) concentrations in 10 to 15 hour-old SHIP2$^{+/+}$, SHIP2$^{+/-}$ and SHIP2$^{-/-}$ newborns injected or not within the first postnatal hour with anti-insulin Ab (⅛₀₀ in 0.9% NaCl, 100 µl per newborn). Values are expressed as the mean ±SEM obtained from the analysis of 9 SHIP2$^{+/+}$, 8 SHIP2$^{+/-}$, 8 SHIP2$^{-/-}$, and 6 anti-insulin Ab-treated SHIP2$^{-/-}$ mice. b, Mortality of SHIP2$^{-/-}$ newborns (n=22/group) injected or not with either D-glucose (7%, 100 µl per injection over the first postnatal day) or a neutralizing guinea pig anti-insulin Ab (⅛₀₀ in 0.9% NaCl, 100 µl within the first postnatal hour). Mann-Whitney tests indicated that mortality of non-treated and treated SHIP2$^{-/-}$ mice was significantly different ($P<0.001$). Mortality of SHIP2$^{-/-}$ newborns treated with either normal guinea pig serum (⅛₀₀ in 0.9% NaCl, 100 µl per newborn) or 0.9% NaCl was not significantly different from non-treated SHIP2$^{-/-}$ mice (data not shown). c, Northern blot analysis of PEPCK, TAT-5' and G-6-Pase expression in liver of 2 to 3.5 hour-old SHIP2$^{+/+}$ and SHIP2$^{-/-}$ newborns treated or not with a single injection of guinea pig anti-insulin Ab within the first hour after birth. The blot was hybridized with a 18S RNA antisense oligonucleotide probe to control for equal loading of total RNA.)
Figure 2B:
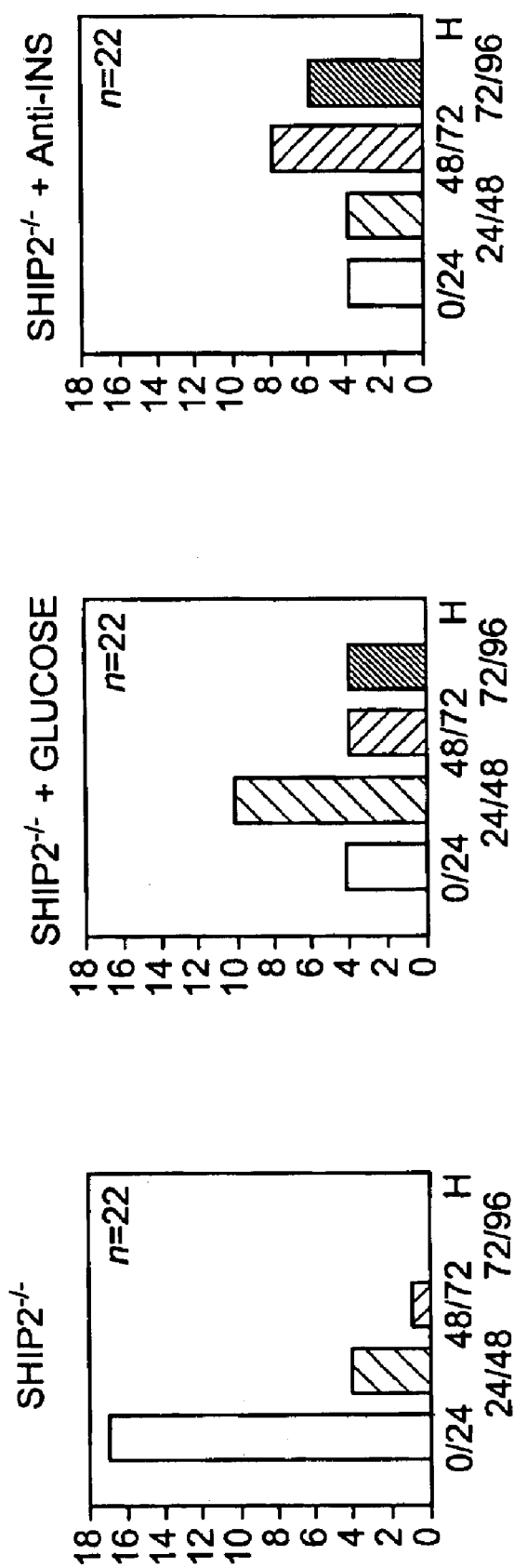

In newborns, severe hypoglycaemia is often associated with cyanotic episodes, apnea, respiratory distress, refusal to feed and somnolence. No difference in blood glucose concentrations among the different genotypes was observed 2 and 8 hours after delivery. However, when analyzed between 10 to 15 hours postpartum, blood glucose concentration in SHIP2$^{-/-}$ mice was significantly lower than in SHIP2$^{+/-}$ and SHIP2$^{+/+}$ mice (FIG. 2a; Student t test, P<10$^{-6}$). Hypoglycaemia was not due to glycosuria nor to an excessive secretion of insulin by the pancreatic beta cells: plasma insulin levels were significantly lower in SHIP2$^{-/-}$ mice than in SHIP2$^{+/-}$ and SHIP2$^{+/+}$ mice (FIG. 2a. Student t test, P<0.05). Histology and immunohistochemistry of pancreatic islets using anti-insulin, -glucagon and -somatostatin antibodies did not reveal any abnormalities of antigen expression and distribution in SHIP2$^{-/-}$ mice. To test whether the hypoglycaemia was the cause of postnatal death, SHIP2$^{-/-}$ mice were injected with D-glucose. Hypoglycaemic SHIP2$^{-/-}$ mice were transiently rescued for up to 96 hours by repeated injections of D-glucose during the first 24 hours postpartum (FIG. 2b). About ten minutes after each injection, SHIP2$^{-/-}$ newborns recovered a normal skin colour and were less lethargic than non-injected mice. Prolonged survival was also observed when SHIP2$^{-/-}$ mice were injected with a neutralizing antibody to insulin within the first hour after birth (FIG. 2b). In addition, anti-Insulin Ab injection of SHIP2$^{-/-}$ mice significantly increased glucose concentrations at 10–15 hours postpartum as compared to non-injected mice (FIG. 2a, Student t test, P<0.0002). These data indicate that hypoglycaemia in SHIP2$^{-/-}$ mice is not caused by an increased production of insulin or decreased glucagon levels, but rather results from an increased sensitivity to insulin.

Figure 2C:
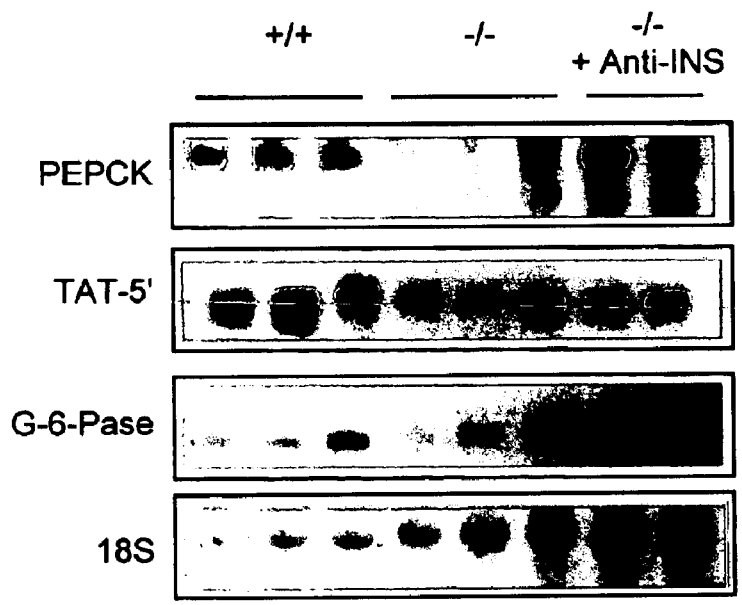

The liver plays a major role in glucose homeostasis at birth: it provides glucose to the blood via gluconeogenesis. During that critical period, transcription of several hepatic enzymes involved in gluconeogenesis is activated in response to hormonal and dietary conditions. Interfering with glucagon or insulin signalling cascades at or just before birth results in delayed or premature appearance of these enzymes, and in neonatal hypoglycaemia or diabetes. Expression of phosphoenolpyruvate carboxykinase (PEPCK), a key enzyme of gluconeogenesis, was very low or absent in liver of SHIP2$^{-/-}$ mice, as compared to SHIP2$^{+/-}$ mice (FIG. 2c). Injection of SHIP2$^{-/-}$ mice with a neutralizing anti-insulin Ab restored a normal expression of PEPCK mRNA (FIG. 2c). Expression of hepatic tyrosine aminotransferase (TAT-5') and glucose-6-phosphatase (G-6-Pase), two other gluconeogenic enzymes also induced after birth, were also decreased, albeit to a lesser extend than PEPCK (FIG. 2c). Levels of C/EBP, C/EBP and aldolase B mRNA were unaffected by the mutation. Thus, the absence of SHIP2 leads to decreased expression of several key gluconeogenic enzymes, contributing to hypoglycaemia in newborn SHIP2$^{-/-}$ mice. Importantly, despite the low insulin levels found in mutant mice, the expression of PEPCK was induced when insulin is neutralized early after birth. Taken together, these data indicate that SHIP2$^{-/-}$ liver cells have enhanced sensitivity to insulin in vivo.

Figure 3A:
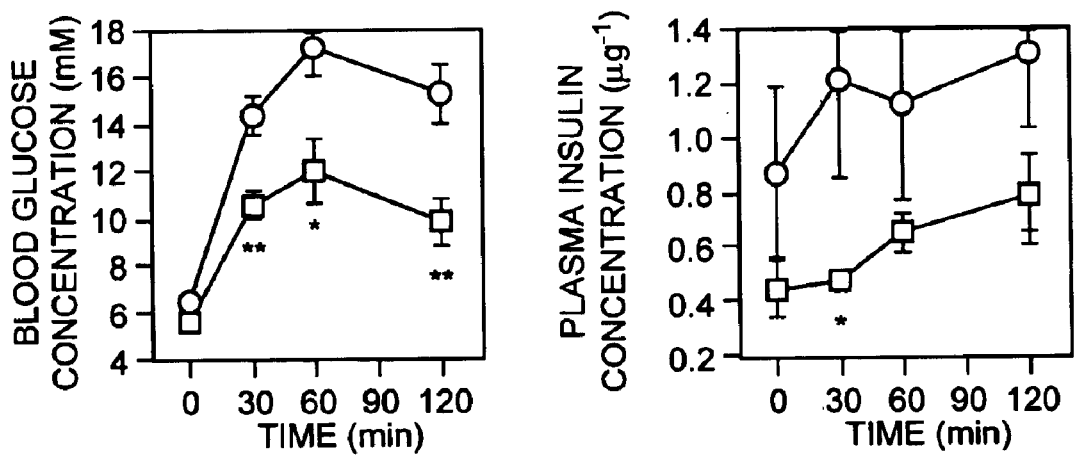
FIG. 3 is showing the increased insulin sensitivity in adult SHIP2$^{+/-}$ mice. (a, Blood glucose (top) and plasma insulin (bottom) concentrations in a glucose tolerance test. Values are expressed as the mean ±SEM obtained from 6 SHIP2$^{+/+}$ (filled circles) and SHIP2$^{+/-}$ (filled squares) mice that have indistinguishable body weight. *$P<0.05$; $P<0.01$ (Student t test). b, Blood glucose concentrations in an insulin tolerance test. Values are expressed as the mean ±SEM obtained from 10 SHIP2$^{+/+}$ (filled circles) and SHIP2$^{+/-}$ (filled squares) mice. $P<0.01$; ***$P<0.001$ (Student t test). c, Northern and Western blot analysis of total RNA and proteins isolated from skeletal muscles of 6–8 week-old SHIP2$^{+/+}$ and SHIP2$^{+/-}$ mice. The Northern blot was hybridized with a mouse SHIP2 cDNA fragment or a 18S RNA antisense oligonucleotide as probes; an anti-SHIP2 Ab was used to detect SHIP2 protein. d, GLUT4 expression in skeletal muscles from adult SHIP2$^{+/+}$ and SHIP2$^{+/-}$ mice. Mice were overnight fasted and injected (insulin) or not (basal) with insulin. The plasma membrane-rich fraction was isolated from myocytes, and GLUT4 levels in this fraction were determined by Western blotting. The results are representative of 3 separate experiments. The amount of GLUT4 was similar in the total lysate prepared from SHIP2$^{+/+}$ and SHIP2$^{+/-}$ myocytes (data not shown). e, Glycogen synthesis in isolated soleus muscles from adult SHIP2$^{+/+}$ and SHIP2$^{+/-}$ mice. Soleus muscles were isolated from overnight fasted male SHIP2$^{+/+}$ and SHIP2$^{+/-}$ mice, and incubated for 60 min without or with (0.1–50 nM) insulin and [$^3$H]-3-Glucose (5 mM, 1 µCi/ml). At the end of the incubation, muscles were dissolved and glycogen was precipitated and counted. Left panel: Values are expressed as nmol glucose incorporated into glycogen per mg muscle protein and are presented as means ±SEM of 7–8 muscles (except at 0,1 nM where 4 muscles were used). * $P<0.02$, ** $P<0.03$ (Student t test). Right panel: Results are expressed as percent of maximal insulin effect (determined by dividing the increment due to insulin at each hormone concentration by the maximal increment in insulin effect at 50 nM).)
Figure 3B:
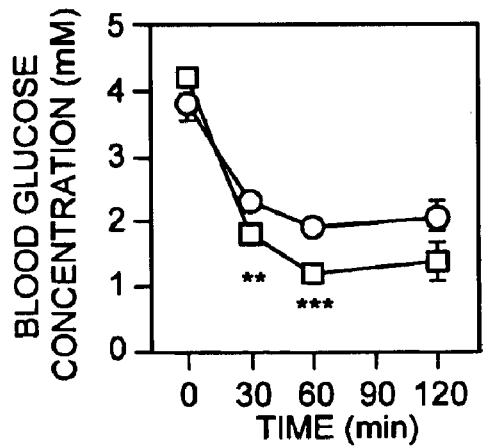

Since SHIP2 is a critical negative regulator of insulin sensitivity in vivo, and since loss of SHIP2 leads to lethal hypoglycaemia in newborn mice, it was investigated whether decreased amounts of SHIP2 expression in SHIP2$^{+/-}$ mice (FIGS. 1c, 1d, 3c) would alter insulin sensitivity. There was no significant difference in basal blood glucose or plasma insulin levels between adult SHIP2$^{+/+}$ and SHIP2$^{+/-}$ mice, either after an overnight fasting (FIG. 3a), or when freely fed (glucose levels in freely fed mice: 9.8±0.5 mM versus 8.8±0.2 mM in SHIP2$^{+/+}$ and SHIP2$^{+/-}$ mice, respectively; insulin levels in freely fed mice: 1.17±0.29 µg/l versus 0.96±0.16 µg/l in SHIP2$^{+/+}$ and SHIP2$^{+/-}$ mice, respectively). However, injection of D-glucose resulted in a more rapid glucose clearance in SHIP2$^{+/-}$ than in SHIP2$^{+/+}$ mice: glycaemia was significantly lower at all time points in SHIP2$^{+/-}$ mice (FIG. 3a). The increased glucose clearance in SHIP2$^{+/-}$ mice was not a consequence of an increased release of insulin: thirty minutes after glucose administration, insulin levels were also significantly lower in SHIP2$^{+/-}$ than in wild-type mice (FIG. 3a). Moreover, the output of insulin from isolated pancreatic islets in response to glucose was not significantly different in SHIP2$^{+/+}$ and SHIP2$^{+/-}$ mice. Insulin hypersensitivity was demonstrated when mice were injected with insulin, that is, a significantly more profound hypoglycaemia was observed by 30 and 60 min after injection in SHIP2$^{+/-}$ mice than in SHIP2$^{+/+}$ mice (FIG. 3b).

Figure 3C:
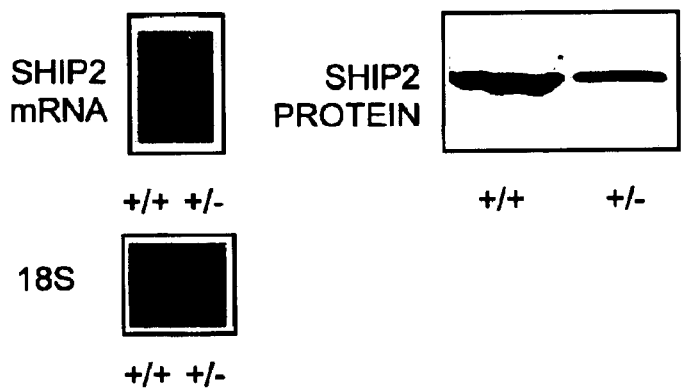
Figure 3D:
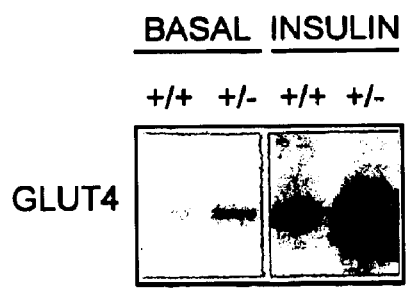
Figure 3E:
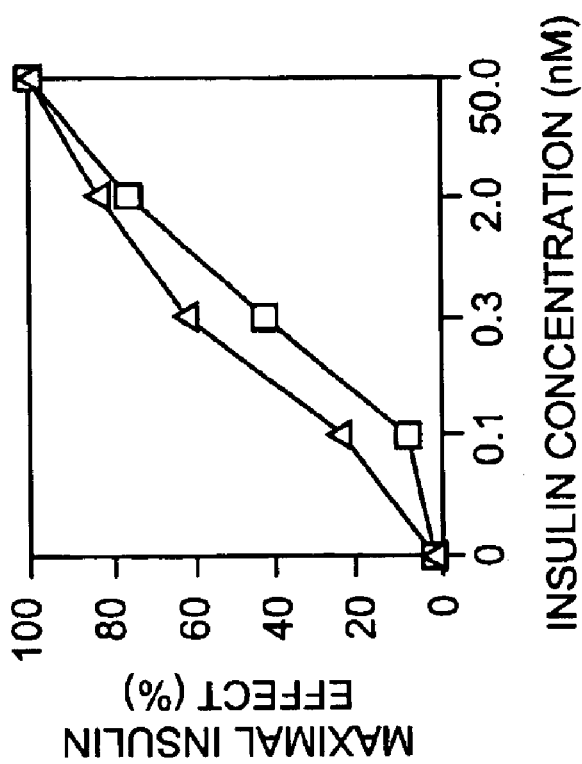
Figure 3E:
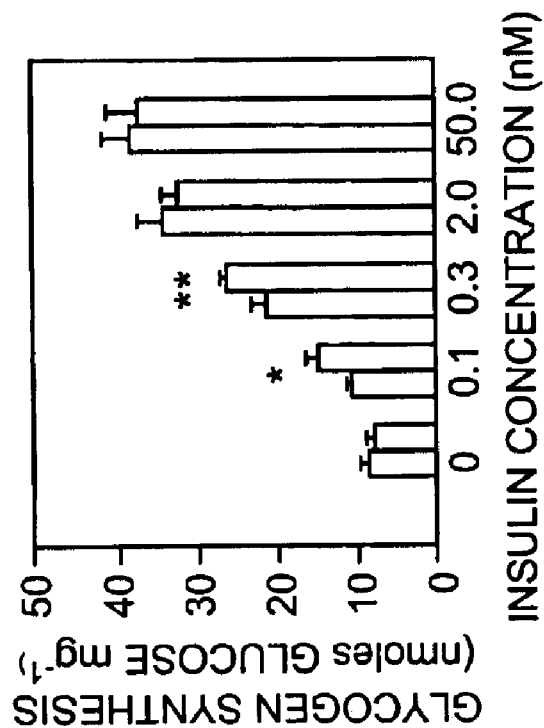

Insulin stimulates glucose transport and storage of glucose as glycogen into skeletal muscles through the translocation of the GLUT4 glucose transporter from intracellular stores to the cell surface (Czech et al. (1999)), and glycogen synthase activation. Loss of one SHIP2 allele resulted in reduced SHIP2 mRNA and protein expression in skeletal muscle cells (FIG. 3c). After an overnight fasting, the amount of GLUT4 transporter in the myocyte plasma membrane fraction was low but similar in SHIP2$^{+/+}$ and SHIP2$^{+/-}$ mice (FIG. 3d). However, when SHIP2$^{+/+}$ and SHIP2$^{+/-}$ mice were loaded with insulin, plasma membrane GLUT4 levels were higher in SHIP2$^{+/-}$ skeletal muscles, consistent with the increased glucose clearance found in these mice. Glycogen synthesis in response to insulin stimulation, which reflects both glucose uptake and glycogen synthase activation, was analyzed in isolated soleus muscles from SHIP2$^{+/-}$ and SHIP2$^{+/+}$ mice (FIG. 3e). In basal condition or in the presence of maximally stimulating insulin concentrations (2 and 50 nM), a similar glycogen synthesis was observed in SHIP2$^{+/+}$ and SHIP2$^{+/-}$ muscles. However, stimulation with lower, physiologic insulin concentrations (0.1 or 0.3 nM) resulted in significantly higher glycogen synthesis in SHIP2$^{+/-}$ muscles than in SHIP2$^{+/+}$ muscles (FIG. 3e). When expressed in percent of maximal insulin effect, the insulin dose response curve was shifted towards the lower insulin concentrations in SHIP2$^{+/-}$ mice, as compared to SHIP2$^{+/+}$ mice (FIG. 3e). Together, data indicate that insulin sensitivity is significantly increased in skeletal muscles from heterozygous mice expressing only reduced amount of SHIP2 protein.

The incidence of adult onset diabetes mellitus has dramatically increased and the disease is a major health care problem. Resistance to the stimulatory effect of insulin on glucose utilization is a key pathogenic feature of most forms of adult onset (type II, or non-insulin dependent) diabetes, and contributes to the morbidity associated with autoimmune (type I, or insulin-dependent) diabetes. It is crucial to better understand the molecular mechanisms that regulate insulin signaling. Data in genetically modified mice identify SHIP2 as a critical and essential negative regulator of insulin signaling and insulin sensitivity in vivo. Thus, SHIP2 is a novel therapeutic target for the treatment of type II diabetes, and a candidate gene predisposing to the same disease.

REFERENCES

1. Pesesse X. et al., *Biochemical and Biophysical Research Communications* 239, 697–700 (1997).
2. Habib, T. et al., *J. Biol. Chem.* 273, 18605–18609 (1998).
3. Pesesse X. et al., *FEBS letters* 437, 301–303 (1998).
4. Wisniewski et al., *Blood* 93, 2707–2720 (1999).
5. Ishihara, H. et al., *Biochem. Biophys. Res. Commun.* 260, 265–272 (1999).
6. Schurmans, S. et al., *Genomics*, in press (1999).
7. Liu, Q. et al., *Blood* 91, 2753–2759 (1998).
8. Czech, M. & Corvera, S., *J. Biol. Chem.* 274, 1865–1868 (1999).
9. Lee, Y. -H. et al., *Mol. Cell. Biol.* 17, 6014–6022 (1997).
10. Bruyns, C. et al., *Biol. Chem.* 380, 969–974 (1999).
11. Simpson, I. A. et al. *Biochim. Biophys. Acta* 763, 393–407 (1983).
12. Higaki, Y. et al., *J. Biol. Chem.* 274, 20791–20795 (1999).
13. Malaisse-Lagae, F. & Malaisse W. J., In: Larner J., Pohl S. L. (eds) Methods in Diabetes Research, vol I, part B. Wiley, New York, pp 147–152 (1984).
14. Stenbit, A. E. et al., *J. Clin. Invest.* 98, 629–634 (1996).
15. Carmeliet et al., *Nature*, Vol. 380, p. 435–439 (1996).
16. Erneux, C. et al., *Biochemica and Biophysica Acta* Vol. 1436, p. 185–199 (1998).

What is claimed is:

1. A method for screening an inhibitor of an inositol polyphosphate 5-phosphatase of SEQ ID No. 1, said method comprising:
   (a) incubating a mixture of inositol polyphosphate substrate and a sample comprising said 5-phosphatase, in the presence and absence of a test compound;
   (b) determining the amount of a 5-phosphatase hydrolysis product formed in the presence and absence of said test compound; and
   (c) comparing the amount of said 5-phosphatase hydrolysis product in the presence of said test compound to the amount of said 5-phosphatase hydrolysis product in the absence of said test compound, wherein a decrease in the amount of a product of 5-phosphatase activity in the presence of the test compound is indicative of said test compound being an inhibitor of said 5-phosphatase.

2. The method of claim 1, wherein said inositol polyphosphate substrate in (a) is a phosphatidylinositol 3,4,5-triphosphate or an inositol 1,3,4,5-tetrakisphosphate.

3. The method of claim 1, wherein said 5-phosphatase hydrolysis product in (b) is a phosphatidylinositol 3,4-diphosphate or an inositol 1, 3, 4-triphasphate.

4. The method of claim 1, wherein said amount of 5-phosphatase hydrolysis product in (b) is determined by thin layer chromatography.

* * * * *

SEQUENCE LISTING

<160> NUMBER OF SEQ ID NOS: 4

<210> SEQ ID NO 1
<211> LENGTH: 1258
<212> TYPE: PRT
<213> ORGANISM: Homo sapiens
<220> FEATURE:
<221> NAME/KEY: SHIP2
<222> LOCATION: (1)..(1258)

-continued

<223> OTHER INFORMATION: amino acid sequence of human Type II SH2-
domain-containing inositol polyphosphate 5-phosphatase or SHIP

<400> SEQUENCE: 1

```
Met Ala Ser Ala Cys Gly Ala Pro Gly Pro Gly Ala Leu Gly Ser
1               5                   10                  15

Gln Ala Pro Ser Trp Tyr His Arg Asp Leu Ser Arg Ala Ala Glu
                20                  25                  30

Glu Leu Leu Ala Arg Ala Gly Arg Asp Gly Ser Phe Leu Val Arg Asp
            35                  40                  45

Ser Glu Ser Val Ala Gly Ala Phe Ala Leu Cys Val Leu Tyr Gln Lys
        50                  55                  60

His Val His Thr Tyr Arg Ile Leu Pro Asp Gly Glu Asp Phe Leu Ala
65                  70                  75                  80

Val Gln Thr Ser Gln Gly Val Pro Val Arg Arg Phe Gln Thr Leu Gly
                85                  90                  95

Glu Leu Ile Gly Leu Tyr Ala Gln Pro Asn Gln Gly Leu Val Cys Ala
            100                 105                 110

Leu Leu Leu Pro Val Glu Gly Glu Arg Glu Pro Asp Pro Pro Asp Asp
            115                 120                 125

Arg Asp Ala Ser Asp Gly Glu Asp Glu Lys Pro Pro Leu Pro Pro Arg
130                 135                 140

Ser Gly Ser Thr Ser Ile Ser Ala Pro Thr Gly Pro Ser Ser Pro Leu
145                 150                 155                 160

Pro Ala Pro Glu Thr Pro Thr Ala Pro Ala Ala Glu Ser Ala Pro Asn
                165                 170                 175

Gly Leu Ser Thr Val Ser His Asp Tyr Leu Lys Gly Ser Tyr Gly Leu
            180                 185                 190

Asp Leu Glu Ala Val Arg Gly Gly Ala Ser His Leu Pro His Leu Thr
            195                 200                 205

Arg Thr Leu Ala Thr Ser Cys Arg Arg Leu His Ser Glu Val Asp Lys
210                 215                 220

Val Leu Ser Gly Leu Glu Ile Leu Ser Lys Val Phe Asp Gln Gln Ser
225                 230                 235                 240

Ser Pro Met Val Thr Arg Leu Leu Gln Gln Gln Asn Leu Pro Gln Thr
                245                 250                 255

Gly Glu Gln Glu Leu Glu Ser Leu Val Leu Lys Leu Ser Val Leu Lys
            260                 265                 270

Asp Phe Leu Ser Gly Ile Gln Lys Lys Ala Leu Lys Ala Leu Gln Asp
            275                 280                 285

Met Ser Ser Thr Ala Pro Pro Ala Pro Gln Pro Ser Thr Arg Lys Ala
290                 295                 300

Lys Thr Ile Pro Val Gln Ala Phe Glu Val Lys Leu Asp Val Thr Leu
305                 310                 315                 320

Gly Asp Leu Thr Lys Ile Gly Lys Ser Gln Lys Phe Thr Leu Ser Val
                325                 330                 335

Asp Val Glu Gly Gly Arg Leu Val Leu Arg Arg Gln Arg Asp Ser
            340                 345                 350

Gln Glu Asp Trp Thr Thr Phe Thr His Asp Arg Ile Arg Gln Leu Ile
            355                 360                 365

Lys Ser Gln Arg Val Gln Asn Lys Leu Gly Val Val Phe Glu Lys Glu
370                 375                 380

Lys Asp Arg Thr Gln Arg Lys Asp Phe Ile Phe Val Ser Ala Arg Lys
385                 390                 395                 400
```

-continued

```
Arg Glu Ala Phe Cys Gln Leu Leu Gln Leu Met Lys Asn Lys His Ser
                405                 410                 415
Lys Gln Asp Glu Pro Asp Met Ile Ser Val Phe Ile Gly Thr Trp Asn
            420                 425                 430
Met Gly Ser Val Pro Pro Lys Asn Val Thr Ser Trp Phe Thr Ser
        435                 440                 445
Lys Gly Leu Gly Lys Thr Leu Asp Glu Val Thr Val Thr Ile Pro His
    450                 455                 460
Asp Ile Tyr Val Phe Gly Thr Gln Glu Asn Ser Val Gly Asp Arg Glu
465                 470                 475                 480
Trp Leu Asp Leu Leu Arg Gly Gly Leu Lys Glu Leu Thr Asp Leu Asp
                485                 490                 495
Tyr Arg Pro Ile Ala Met Gln Ser Leu Trp Asn Ile Lys Val Ala Val
                500                 505                 510
Leu Val Lys Pro Glu His Glu Asn Arg Ile Ser His Val Ser Thr Ser
                515                 520                 525
Ser Val Lys Thr Gly Ile Ala Asn Thr Leu Gly Asn Lys Gly Ala Val
            530                 535                 540
Gly Val Ser Phe Met Phe Asn Gly Thr Ser Phe Gly Phe Val Asn Cys
545                 550                 555                 560
His Leu Thr Ser Gly Asn Glu Lys Thr Ala Arg Arg Asn Gln Asn Tyr
                565                 570                 575
Leu Asp Ile Leu Arg Leu Leu Ser Leu Gly Asp Arg Gln Leu Asn Ala
                580                 585                 590
Phe Asp Ile Ser Leu Arg Phe Thr His Leu Phe Trp Phe Gly Asp Leu
            595                 600                 605
Asn Tyr Arg Leu Asp Met Asp Ile Gln Glu Ile Leu Asn Tyr Ile Ser
            610                 615                 620
Arg Lys Glu Phe Glu Pro Leu Leu Arg Val Asp Gln Leu Asn Leu Glu
625                 630                 635                 640
Arg Glu Lys His Lys Val Phe Leu Arg Phe Ser Glu Glu Ile Ser
                645                 650                 655
Phe Pro Pro Thr Tyr Arg Tyr Glu Arg Gly Ser Arg Asp Thr Tyr Ala
                660                 665                 670
Trp His Lys Gln Lys Pro Thr Gly Val Arg Thr Asn Val Pro Ser Trp
            675                 680                 685
Cys Asp Arg Ile Leu Trp Lys Ser Tyr Pro Glu Thr His Ile Ile Cys
            690                 695                 700
Asn Ser Tyr Gly Cys Thr Asp Asp Ile Val Thr Ser Asp His Ser Pro
705                 710                 715                 720
Val Phe Gly Thr Phe Glu Val Gly Val Thr Ser Gln Phe Ile Ser Lys
                725                 730                 735
Lys Gly Leu Ser Lys Thr Ser Asp Gln Ala Tyr Ile Glu Phe Glu Ser
                740                 745                 750
Ile Glu Ala Ile Val Lys Thr Ala Ser Arg Thr Lys Phe Phe Ile Glu
            755                 760                 765
Phe Tyr Ser Thr Cys Leu Glu Glu Tyr Lys Lys Ser Phe Glu Asn Asp
    770                 775                 780
Ala Gln Ser Ser Asp Asn Ile Asn Phe Leu Lys Val Gln Trp Ser Ser
785                 790                 795                 800
Arg Gln Leu Pro Thr Leu Lys Pro Ile Leu Ala Asp Ile Glu Tyr Leu
                805                 810                 815
```

-continued

Gln Asp Gln His Leu Leu Leu Thr Val Lys Ser Met Asp Gly Tyr Glu
              820                 825                 830

Ser Tyr Gly Glu Cys Val Val Ala Leu Lys Ser Met Ile Gly Ser Thr
          835                 840                 845

Ala Gln Gln Phe Leu Thr Phe Leu Ser His Arg Gly Glu Thr Gly
    850                 855                 860

Asn Ile Arg Gly Ser Met Lys Val Arg Val Pro Thr Glu Arg Leu Gly
865                 870                 875                 880

Thr Arg Glu Arg Leu Tyr Glu Trp Ile Ser Ile Asp Lys Asp Glu Ala
              885                 890                 895

Gly Ala Lys Ser Lys Ala Pro Ser Val Ser Arg Gly Ser Gln Glu Pro
              900                 905                 910

Arg Ser Gly Ser Arg Lys Pro Ala Phe Thr Glu Ala Ser Cys Pro Leu
          915                 920                 925

Ser Arg Leu Phe Glu Glu Pro Glu Lys Pro Pro Thr Gly Arg Pro
    930                 935                 940

Pro Ala Pro Pro Arg Ala Ala Pro Arg Glu Glu Pro Leu Thr Pro Arg
945                 950                 955                 960

Leu Lys Pro Glu Gly Ala Pro Glu Pro Glu Gly Val Ala Ala Pro Pro
              965                 970                 975

Pro Lys Asn Ser Phe Asn Asn Pro Ala Tyr Tyr Val Leu Glu Gly Val
              980                 985                 990

Pro His Gln Leu Leu Pro Pro Glu Pro Pro Ser Pro Ala Arg Ala Pro
          995                 1000                1005

Val Pro Ser Ala Thr Lys Asn Lys Val Ala Ile Thr Val Pro Ala
    1010                1015                1020

Pro Gln Leu Gly His His Arg His Pro Arg Val Gly Glu Gly Ser
    1025                1030                1035

Ser Ser Asp Glu Glu Ser Gly Gly Thr Leu Pro Pro Pro Asp Phe
    1040                1045                1050

Pro Pro Pro Pro Leu Pro Asp Ser Ala Ile Phe Leu Pro Pro Ser
    1055                1060                1065

Leu Asp Pro Leu Pro Gly Pro Val Val Arg Gly Arg Gly Gly Ala
    1070                1075                1080

Glu Ala Arg Gly Pro Pro Pro Lys Ala His Pro Arg Pro Pro
    1085                1090                1095

Leu Pro Pro Gly Pro Ser Pro Ala Ser Thr Phe Leu Gly Glu Val
    1100                1105                1110

Gly Ser Gly Asp Asp Arg Ser Cys Ser Val Leu Gln Met Ala Lys
    1115                1120                1125

Thr Leu Ser Glu Val Asp Tyr Ala Pro Ala Gly Pro Ala Arg Ser
    1130                1135                1140

Ala Leu Leu Pro Gly Pro Leu Glu Leu Gln Pro Pro Arg Gly Leu
    1145                1150                1155

Pro Ser Asp Tyr Gly Arg Pro Leu Ser Phe Pro Pro Arg Ile
    1160                1165                1170

Arg Glu Ser Ile Gln Glu Asp Leu Ala Glu Ala Pro Cys Leu
    1175                1180                1185

Gln Gly Gly Arg Ala Ser Gly Leu Gly Glu Ala Gly Met Ser Ala
    1190                1195                1200

Trp Leu Arg Ala Ile Gly Leu Glu Arg Tyr Glu Glu Gly Leu Val
    1205                1210                1215

His Asn Gly Trp Asp Asp Leu Glu Phe Leu Ser Asp Ile Thr Glu

```
    1220                1225                1230
Glu Asp Leu Glu Glu Ala Gly Val Gln Asp Pro Ala His Lys Arg
    1235                1240                1245
Leu Leu Leu Asp Thr Leu Gln Leu Ser Lys
    1250                1255

<210> SEQ ID NO 2
<211> LENGTH: 28
<212> TYPE: DNA
<213> ORGANISM: Artificial Sequence
<220> FEATURE:
<223> OTHER INFORMATION: primer
<221> NAME/KEY: Oligonucleotide
<222> LOCATION: (1)..(28)

<400> SEQUENCE: 2
cagaccatta tgcagctgag gaggcatt                                  28

<210> SEQ ID NO 3
<211> LENGTH: 21
<212> TYPE: DNA
<213> ORGANISM: Artificial Sequence
<220> FEATURE:
<223> OTHER INFORMATION: primer
<221> NAME/KEY: Oligonucleotide
<222> LOCATION: (1)..(21)

<400> SEQUENCE: 3
gtgcgtactt agacatgcat g                                         21

<210> SEQ ID NO 4
<211> LENGTH: 10
<212> TYPE: PRT
<213> ORGANISM: Homo sapiens
<220> FEATURE:
<221> NAME/KEY: short amino acid sequence of SHIP-2
<222> LOCATION: (1)..(10)

<400> SEQUENCE: 4

Arg Thr Asn Val Pro Ser Trp Cys Asp Arg
1               5                   10
```